United States Patent [19]

Gale

[11] Patent Number: 4,834,979
[45] Date of Patent: * May 30, 1989

[54] MEDICAL BANDAGE FOR ADMINISTERING BENEFICIAL DRUG

[75] Inventor: Robert M. Gale, Los Altos, Calif.

[73] Assignee: ALZA Corporation, Palo Alto, Calif.

[*] Notice: The portion of the term of this patent subsequent to Dec. 4, 2001 has been disclaimed.

[21] Appl. No.: 132,827

[22] Filed: Dec. 14, 1987

Related U.S. Application Data

[62] Division of Ser. No. 278,364, Jun. 29, 1981, Pat. No. 4,725,272.

[51] Int. Cl.$^4$ .............................................. A61F 13/02
[52] U.S. Cl. .................................. 424/448; 424/449; 424/447
[58] Field of Search .................. 424/449, 448, 447

[56] References Cited

U.S. PATENT DOCUMENTS

| | | | |
|---|---|---|---|
| 3,028,307 | 4/1962 | Niger | 167/82 |
| 3,048,262 | 4/1976 | Zaffaroni | 128/260 |
| 3,063,900 | 11/1962 | Winsor | 167/65 |
| 3,096,242 | 7/1963 | Young | 167/65 |
| 3,428,728 | 2/1969 | Lowey | 424/14 |
| 3,598,122 | 8/1971 | Zaffaroni | 424/449 |
| 3,598,123 | 8/1971 | Zaffaroni | 424/449 |
| 3,734,097 | 5/1973 | Zaffaroni | 424/449 |
| 3,742,951 | 7/1973 | Zaffaroni | 424/449 |
| 3,789,119 | 1/1974 | Fusari et al. | 424/78 |
| 3,797,494 | 3/1974 | Zaffaroni | 424/449 |
| 3,896,819 | 7/1975 | Zaffaroni | 128/230 |
| 3,921,636 | 11/1975 | Zaffaroni | 128/260 |
| 3,980,084 | 9/1976 | Kross | 128/283 |
| 3,996,934 | 12/1976 | Zaffaroni | 128/268 |
| 4,014,335 | 3/1977 | Arnold | 128/260 |
| 4,031,894 | 6/1977 | Urquhart et al. | 424/449 |
| 4,060,084 | 11/1977 | Chandrasekaran et al. | 128/260 |
| 4,262,003 | 4/1981 | Urquhart et al. | 424/267 |
| 4,286,592 | 9/1981 | Chandrasekaran | 424/449 |
| 4,329,333 | 5/1982 | Barr | 424/19 |
| 4,350,785 | 9/1982 | Habib | 524/55 |
| 4,486,193 | 12/1984 | Shaw et al. | 424/449 |
| 4,650,484 | 3/1987 | Shaw et al. | 424/449 |
| 4,725,272 | 2/1988 | Gale | 424/449 |

FOREIGN PATENT DOCUMENTS 0013606 4/1980 European Pat. Off. .

OTHER PUBLICATIONS

Rochow, Introduction to the Chemistry of the Silicones, 2nd Ed., John Wiley and Sons, Inc., New York, pp. 88–90, 94–95 (1946, 1951).
Kirk-Othmer, Encyclopedia of Chemical Tech., vol. 10, 3rd Ed., John Wiley and Sons, New York, pp. 216–232 (1980).
Goodman, The Pharmacological Basis of Therapeutics, 4th Edition, p. 752, (1970).
Burch, Am. Heart J., p. 842, (1966).
Casky. Handbook of Pharmacology, 6th Edition, pp. 241–243, (1979).
Baines, J. Pharm. Sci., vol. 57, pp. 893–94, (1986).
Merck, The Merck Index, p. 965 (1968).
Pauling, The Nature of the Chemical Bond,, p. 495, (1960).
Boehn, Angewandte Chemie, Intl. Ed., vol. 5, pp. 533–541, (1966).
Cabot (Advertisements Cab-O-Sil) pp. 4, 9, 12 & 18, (1979).
Parkyns, Cata Proc. Int. Congr., 5th, vol. 12, pp. 255 & 261, (1973).

Primary Examiner—Thurman K. Page
Assistant Examiner—L. Horne
Attorney, Agent, or Firm—Paul L. Sabatine; Edward L. Mandell; Steven F. Stone

[57] ABSTRACT

A medical bandage is disclosed comprising a reservoir containing a gelled fluid, rheological agent and a drug. A method of using the bandage for producing a beneficial effect is disclosed also.

9 Claims, 2 Drawing Sheets

MEDICAL BANDAGE FOR ADMINISTERING BENEFICIAL DRUG

CROSS-REFERENCE TO RELATED APPLICATION

This application is a division of U.S. Pat. Appln. Ser. No. 06/278,364 filed June 29, 1981, now U.S. Pat. No. 4,725,272 issued Feb. 16, 1988, which appln. is incorporated herein by reference and benefit is claimed of its filing date; this appln. also is copending with U.S. applns. identified by atty's docket No. ARC 788 Div. 1 now U.S. Appln. Ser. No. 07/132,829 filed Dec. 14, 1987, ARC 788 Div. 2 now U.S. Appln. Ser. No. 07/132,828 filed Dec. 14, 1987 and ARC 788 Cont. 2 now U.S. Appln. Ser. No. 07/132,832 filed Dec. 14, 1987.

FIELD OF THE INVENTION

This invention pertains to a medical bandage. More particularly, the invention relates to a medical bandage for administering a drug to the skin over a prolonged period of time. The invention also relates to a method for administering the drug percutaneously using the medical bandage.

BACKGROUND OF THE INVENTION

Medical bandages for administering a drug, for example a vasodilator, to the skin are known to the prior art. For example, in U.S. Pat. No. 3,742,951 as issued to Zaffaroni, there is disclosed a medical bandage comprising a backing member defining one surface of the bandage, a pressure sensitive adhesive defining the other surface of the bandage, and disposed between the surfaces a drug reservoir. The reservoir in one embodiment is a solid matrix formed of polymeric material having the drug dispersed therein. The polymeric matrix is permeable to the passage of drug and it releases it to a rate controlling membrane for metering the flow of drug from the device.

In U.S. Pat. No. 3,797,494 issued to Zaffaroni, there is described a medical bandage for administering drug percutaneously in which the drug may be mixed with a transport agent that enhances the penetration of the skin by the drug. The main components of this bandage are a backing member, a drug reservoir layer, a microporous membrane, and a contact adhesive layer. The patent indicates the rate of drug administration is controlled by the rate at which drug diffuses from the reservoir through the microporous membrane. In U.S. Pat. No. 3,996,934 issued to Zaffaroni, a medical bandage is disclosed comprising a backing member, a reservoir, a release rate controlling membrane, and a fastening system for securing the bandage to the patient.

In U.S. Pat. Nos. 4,031,894 and 4,262,003, patentee Urquhart et al disclosed a medical bandage comprising a reservoir of mineral oil and polyisobutene. The polyisobutene is used for imparting gel and adhesive properties to the reservoir. In U.S. Pat. No. 4,060,084, patentees Chandrasekaran et al disclosed a medical bandage used for providing chemotherapy transdermally by administering an initial dose followed by a constant dose.

While the above described medical bandages respresent an advancement in the drug delivery art, it will be appreciated a further advancement in medical bandages can be made by providing a medical bandage that can deliver drugs from low to high diffusion rates, and at a substantialy constant rate useful for the management of medical situations where such need occurs.

OBJECTS OF THE INVENTION

Accordingly, it is an object of this invention to provide a medical bandage for enhanced continuous administration of therapeutically effective amounts of drugs to the skin over a period of time.

Another object of the invention is to provide a reliable and easy to use medical bandage for continuously administering controlled amounts of drugs through the skin.

It is a further object of this invention to provide a medical bandage for the transdermal delivery of a drug, particularly a vasodilator, and which medical bandage is compatible with the skin and administers the drug at a substantially constant rate up to high therapeutically effective dosages over time.

Other objects, features and advantages of this invention will be apparent to those skilled in the art from the detailed description of the invention, the drawings and the accompanying claims.

BRIEF DESCRIPTION OF THE DRAWINGS

In the drawings, which are not drawn to scale, but are set forth for illustrating the invention, the drawings are as follows.

DETAILED DESCRIPTION OF THE INVENTION

In accordance with this invention, there is provided a medical bandage containing a useful drug that is administered in a controlled therapeutically effective and beneficial amount to the skin of an animal, particularly the skin of a human patient over a prolonged period of time.

Figure 1:
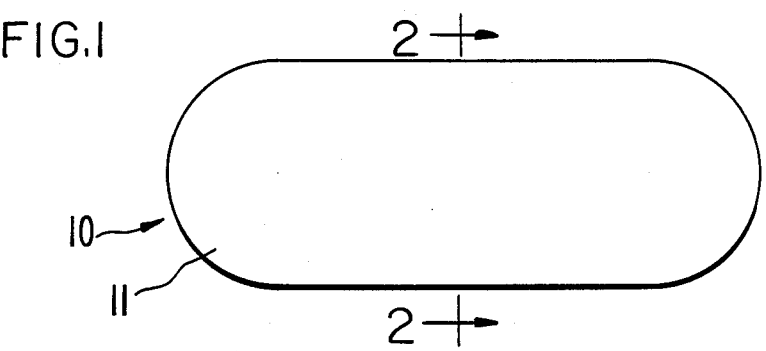
FIG. 1 is a top view of a medical bandage provided by the invention.

FIG. 1 illustrates a medical bandage 10 that is designed and adapted for easy placement and comfortable retention on the skin. Medical bandage 10 can be shaped and sized for placement and retention on various anatomic regions for percutaneous administration of a drug to a patient. The anatomic regions for transdermally administering drug are represented by the forearms, abdomen, chest, back, thigh, buttock and the like. Medical bandage 10 can have various shapes, such as oblong, as seen in FIG. 1, or medical bandage 10 can be square, rectangular, round, convex in appearance, and the like. FIG. 1 is a top view of medical bandage 10, and it is the structural backing member 11 of bandage 10. The term top is used to indicate the visual side of the bandage, which side is positioned distant from a skin receptor when the bandage is used for its intended purpose.

Figure 2:
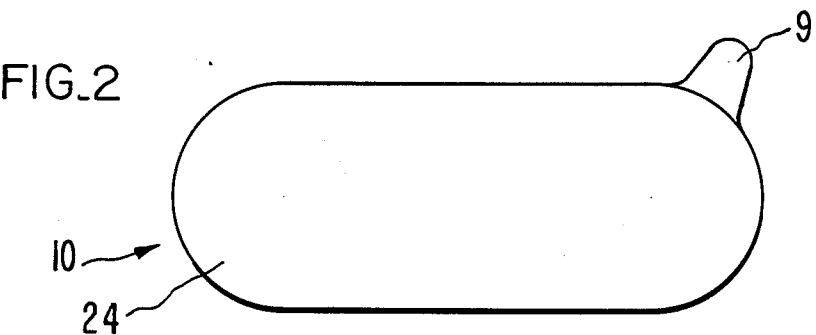
FIG. 2 is a bottom view of the medical bandage made with a pull tab for removing a release liner prior to use.

FIG. 2 illustrates the bottom of medical bandage 10. The term bottom indicates the side of the bandage placed in contact with a skin receptor site for administering drug through the skin. In FIG. 2, the bottom of bandage 10 illustrated is a release liner 24. The release liner is made preferrably with a pull tab 9 for pulling the liner from the bandage just prior to use. The release liner also can be made without the tab, and it is stripped free of medical bandage 10 immediately before use.

Figure 3:
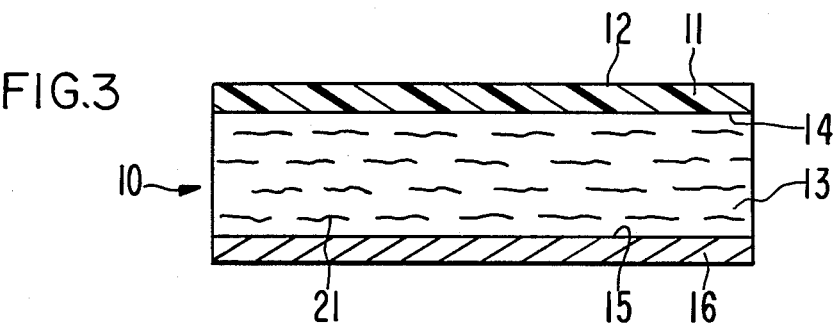
FIG. 3 is a cross-sectional view of the medical bandage of FIG. 1 as seen through 2—2 of FIG. 1.
Figure 4:
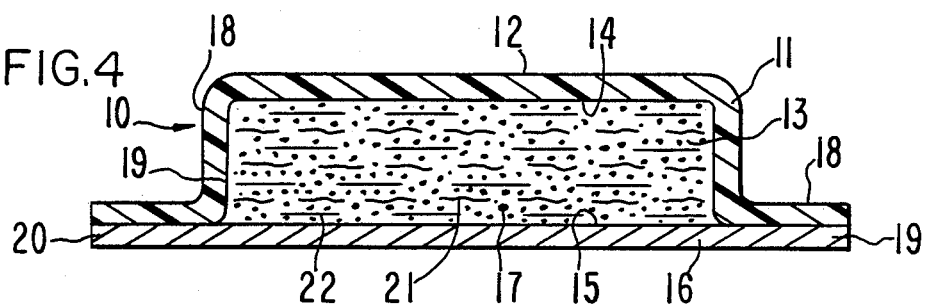
FIG. 4 is an embodiment of the medical bandage of FIG. 1 as seen in opened section.
Figure 5:
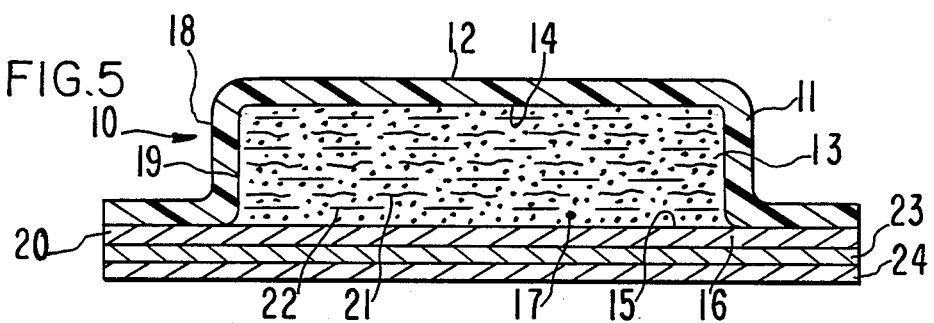
FIG. 5 is a medical bandage seen in opened structure with the bandage defining a means for placing the bandage on the patient.

FIGS. 3, 4, and 5 are cross sectional embodiments of medical bandage 10 of FIG. 1, and they are seen in openedsection for illustrating the structure of bandage 10. In FIGS. 3, 4, and 5, bandage 10 comprises a backing member 11 that defines the top of bandage 10. Backing member 11 serves as a protective cover for bandage 10, it imparts structural support to the bandage, and it substantially keeps components in bandage 10 from escaping the bandage. Backing member 11 is made from a material 12 that is substantially impermeable to the components in bandage 10, or member 11 is made from a combination of materials such as a composite, or a laminate to yield a backing member that is substantially impermeable to the passage of components in bandage 10. Representative examples of materials used for manufacturing medical bandage 10 are presented later in the disclosure.

A reservoir 13, adjacent to backing member 11, is positioned immediately below and in contact with one surface 14 of backing member 11. Reservoir 13 bears on its surface distant from backing member 11 a membrane 16 for controlling the release of drug 17, represented by dots, from medical bandage 10. In the bandage as seen in FIGS. 4 and 5, outer edges 18 of backing member 11 will overlay edges 19 of reservoir 13, and they will be joined along these perimeters in a fluid tight arrangement. This sealed reservoir is effected by pressure, fusion, adhesion or through an adhesive applied to the edges of the membrane. In this structure, reservoir 13 is contained wholly between backing member 11 and release rate controlling membrane 16, and reservoir 13 does not in this manufacture have any exposed surfaces. In a preferred embodiment, backing member 11 and release rate controlling membrane 16 will be inherently sealable to each other, or they will include a sealing means, such as a film positioned between and sealable to both the backing member and the release rate controlling membrane, or by a layer of an adhesive. Reservoir 13 comprises a continuous phase as represented by wavy lines 21, and it is formed of a fluid to viscous material permeable to the passage of drug 17. A description of which follows in the disclosure. Reservoir 13 also contains a rheology agent 22, represented by dashes. Reservoir 13 contains a dosage unit amount of drug 17 that is supplied to release rate controlling membrane 16 throughout the medical history of bandage 10. The dosage amount comprises a supply of drug for one hour, for eight hours for a normal night sleep, for 24 hours applied once daily, for 48 hours or longer. In practicing the therapeutic method of drug administration, a single medical bandage can be on the skin, more than one medical bandage can be on the skin, and the medical bandage can be applied topically successively for the intended result.

Rate controlling membrane 16 has one surface in contact with reservoir 13. Membrane 16, adjacent to reservoir 13, is formed of a material that is dense or microporous, and it is a polymeric material that controls the rate of drug release from reservoir 13. Membrane 16 permits the passage of drug 17 at a rate dependent on the solubility of drug therein, as well as on the thickness of the membrane. The dosage rate per area of medical bandage 10, or the flux of drug, thus is controlled to the exterior of the bandage by regulating the composition, thickness of membrane 16 and the diffusion coefficient of the drug. Medical bandage 10 can be provided with the same surface area and having different dosage of drug release by varying the characteristics of membrane 16. Diffusion coefficients can be determined by standard techniques.

Medical bandage 10 further comprises a layer or lamina of an adhesive 23 in contact with the releasing surface of membrane 16, that is, it is directly below and adjacent to membrane 16, or optionally adhesive 23 extends around the outer perimeter of membrane 16. Contact adhesive layer 23 is the presently preferred means by which bandage 10 is affixed to a warm-blooded animal, mainly to the area of the skin selected for receiving the drug. The composition and the thickness of adhesive layer 23 are such that layer 23 does not constitute a significant permeation barrier to the passage of drug, and it should preferably be substantially more permeable to the passage of drug than membrane 16, and it is at least as permeable to drug as membrane 16. The adhesive used for the present purpose are dermatologically acceptable and it permits the bandage to be easily removed from the skin after the period of drug administration.

Medical bandage 10 also may include a release liner 24 in contact with adhesive layer 23. Release liner 24 protects the bandage, and just prior to use it is pulled away from adhesive layer 23 and discarded. Release liner 24 is made from a material that is substantially impermeable to the passage of drug. The same material used for backing member 11 may be used to make release liner 24 provided they are strippable materials and compatible with medical bandage 10. In a preferred embodiment, the release liner is made with a pull tab to facilitate removal of the liner from bandage 10 before use.

Turning to materials used for manufacture of medical bandage 10, and more specifically to backing member 11, backing member 11 comprises occlusive and non-occlusive, flexible and non-flexible materials. Examples of materials that can be used as backing member 11 are polymeric materials such as low to high density polyethylene, polypropylene, polyethylene terephthalate, nylon, and the like. Also, the backing materials include metal foil used alone, such as aluminum, or metal foil laminated to a polymeric substrate for added strength and toughness. In a presently preferred embodiment, backing member 11 is a composite designed for strength and as a barrier for preventing loss of drug. Multilaminated films also can serve as a backing member comprising a lamina of medium density polyethylene in laminar arrangement with a lamina formed of the polyester polyethylene terephthalate on which a thin layer of aluminum was vapor deposited, and a lamina formed of the copolymer ethylene-vinyl acetate. The combined lamina of aluminum and the polyester makes the film substantially a total barrier to the passage of diffusing drug. The use of ethylene-vinyl acetate copolymer enables the multilaminate to be sealed to the other membranes comprising the medical bandage. Siliconized polymers, such as siliconized polyalkylene terephthalate also can be used, alone, or in the laminate. The backing member also includes a laminate comprising a lamina of polyethylene terephthalate on which aluminum is vapor deposited, which is adhered to a lamina formed of ethylene-vinyl acetate copolymer through an intermediate binding agent such as a polyurethane adhesive, or an ionomer sold as Surlyn ® by DuPont. Ionomer refers to a class of polymers in which ionized carboxyl groups create ionic cross-links in the intermolecular structures. Ionomers include polyacrylic acids, polyalkylacrylic acids, polymethacrylic acid, polyethacrylic acid, polyacrylamides, polyolefins, and the like. Ionomers are described in *Encylcopedia of Polymer Science And Technology*, Vol. 6, pages 420 to 431, 1967, and in *Encyclopedia of Chemical Technology*, Vol. 10, page 229, 1980.

The materials forming reservoir 13 of medical bandage 10 comprise a continuous phase formed of a fluid containing a rheological agent and a drug. Generically, the term fluid as used for the purpose of this invention includes naturally occurring and synthetic oils. The oils are selected from the group consisting essentially of organic and inorganic oils, such as animal, fruit, marine, mineral, nut, plant, sylvan and vegetable oils. Exemplary oils are liver, herring, whale, babassu, almond, peanut, sesame, castor, cottonseed, olive, palm, rapeseed, corn, soybean, eucalyptus and tung oils. In a preferred embodiment, silicone fluid, also called silicone oil, is used for forming the reservoir because drugs can be easily mixed into the fluid at high drug loading, the fluid is permeable to the passage of drugs, it is compatible with drugs and drugs are stable in the fluid so the bandage can be stored essentially free of drug degradation. The fluid is essentially impermeable in the backing member and the rate controlling membrane, thereby avoiding migration of fluid from the reservoir. The silicone fluids are nontoxic, nonallergenic and physiologically inert. The silicone fluids are commercially available in a range of viscosities from inviscid to viscous, and they can exhibit newtonian to nonnewtonian behavior. They are available in a range of viscosities, namely from 1 to 100,000 centistokes, cts, and higher. The use of silicone fluids possessing high viscosities facilitates the manufacture of the bandage because there is less opportunity for the higher viscosity fluids to flow during sealing procedures. Representative silicone fluids include dimethylsilicone fluid, methylphenylsiloxysilicone fluid, diphenylsiloxysilicone fluid, methylvinylsiloxysilicone fluid, methyltrifluoropropylsilicone fluid, polydimethysiloxane fluid, and the like. The amount of fluid present in the reservoir is about 10 to 90 wt %, and more preferably about 30 to 65 wt %.

The rheological agent is added to the reservoir for its thixotropic and thickening properties. The agent is used as an aid in forming the continuous phase, for modifying, usually for reducing the ability of the fluid to flow which results in an increased viscosity of the continuous phase and for gelling the fluid. The agent also is used for essentially eliminating slump, or run in the reservoir leading to controlled release from the bandage, and for preventing settling of drug during storage. The combination of the fluid, for example a silicone oil, and the rheological agent leads to a reservoir, comprising in a presently preferred embodiment, a gel, that can release drug at low to high diffusion rates while releasing the drug at substantially zero order rates, a reservoir that is hydrophobic for increasing the stability of certain drugs, and a reservoir that exhibits a decreased viscosity. Representative rheologic agents are naturally occurring or of synthetic origin. They are selected from the group consisting of cellulosic, polysaccharide and silicone agents. Exemplary polysaccharides include linear or branched polysaccharides, or a polysaccharide with basic, carboxyl or other acid groups. Typical polysaccharide agents include agar, agarose, algin, sodium alginate, potassium alginate, carrageenan, kappa-carrageenan, lambda-carrageenan, fucoidan, furcellaran, laminaran, hypnea, eucheuma, gum arabic, gum ghatti, gum karaya, gum tragacanth, guar gum, locust bean gum, quince psyllium, okra gum, arabinoglactin, perctin, xanthan, scleroglucan, dextran, amylose, amylosepectin, dextrin and the like. The cellulose agents include cellulose, cellulose derivatives, alkylcellulose, hydroxyalkylcellulose derivatives wherein the alkyl group it 1 to 7 carbons, carboxyalkylcellulose, and the alkali metal derivatives thereof. Exemplary rheological cellulose agents include substituted and unsubstituted celluloses, such as cellulose, methyl cellulose, ethyl cellulose, propyl cellulose, hydroxyproply cellulose, hydroxyethyl cellulose, sodium carboxymethyl cellulose, and the like. The presently preferred rheological agents include compounds containing silicone such as fumed silica, reagent grade sand, precipitated silica, amorphous silica, colloidal silicon dioxide, fused silica, silica gel, quartz and particulate siliceous materials commercially available as Syloid ®, Cabosil ®, Aerosil ®, and Whitelite ®. The amount of silicone compound used for the present purpose usually is about 0.1% by weight to 25% by weight, and more preferably 1% to 10% by weight of the total reservoir.

The drugs that can be incorporated into reservoir 13 comprise drugs that can be administered percutaneously through skin for passage into the systemic circulation. In a presently preferred embodiment, the drugs are vasodilators, with a more preferred group of vasodilators including nitrites, nitrates, and their esters, such as their esters of sugars and polyols. The vasodilators generally possess a member selected from the group consisting of ONO and $ONO_2$. Those drugs include amyl nitrite, glyceryl trinitrate, also known as nitroglycerin, nitroglycerin absorbed on lactose such as 1 to 30% nitroglycerin on 99 to 70% lactose, preferably 10% nitroglycerin absorbed on beta-lactose or optionally on alphalactose. The vasodilator nitroglycerin readily permeates through human skin. The results of transdermal flux measurements in vitro indicate a range of 10–12 $\mu g/cm^2$-hr at 30° C. and of 75–90 $\mu g/cm^2$-hr at 37° C. Generally, the therapeutic release rate for a typical medical bandage provided by the invention for administering nitroglycerin is a flux of 10–2000 $\mu g/hr$, with an average releasing surface of 5–50 $cm^2$. A preferred embodiment for a bandage releasing nitroglycerin is about 20 to 1200 $\mu g/hr\text{-}cm^2$. Other vasodilators useful for the present purpose of octyl nitrite, sodium nitrite, clonitrate, erythrityl tetranitrate, isosorbide dinitrate, mannitol hexanitrate, pentaerythritol tetranitrate, pentrintrol, triethanolamine trinitrate, trolnitrate phosphate (triethanolamine trinitrate diphosphate), and the like. The amount of drug in the reservoir ranges from about 0.1% by weight to about 70% by weight, for a vasodilator the drug loading in the reservoir is a dosage unit amount or enough for carrying out a medical program, and it is about 1% to 40% by weight, usually, about 5 mg to 1000 mg of vasodilator. The vasodilators are used to relieve the pain associated with angina pectoris, for the prevention of angina, in hypertension, for relaxation of involuntary muscles of blood vessels mainly arteries and arterioles, for increasing the flow of blood therein, and for increasing oxygenation from vasodilation, mainly for increasing the supply of oxygen to the heart. The bandage can be worn continuously for lessening the incidence of angina pectoris, particularly nocturnal angina. The drugs are known in *Cutting's Handbook of Pharmacology*, Sixth Edition, Chapter 24, 1979.

Membrane 16, is a release rate controlling polymeric material for governing the amount of drug released from medical bandage 10, over time. The membrane can be selected to deliver drug at a rate less than the permeability of the skin, or the membrane can be chosen to deliver drug at a rate slightly above the permeability rate of average skin. The use of a membrane that delivers drug at a slightly higher flux than the skin, or dermis, makes possible minimizing the bandage size required for most of the clinical population. Release rate membrane 16 also assures the constant maintenance of a controlled release rate for initiation of the drug administration period and beyond a 24 hour period. Moreover, in the case of extremely permeable skin, membrane 16 has the function of a safety membrane that restricts the delivery of drug to the mammalian skin. Representative polymers for forming rate controlling membrane 16 include polyolefins such as polyethylene and polypropylene, polyamides, polyester, ethylene-ethacrylate copolymer, segmented copolymer of butylene terephthalate 33% and polytetramethylene ether terephthalate 67%, segmented copolymer of propylene terephthalate 58% and polytetramethylene ether terephthalate, block copolymer of tetramethylene terephthalate-polytetramethylene ether glycol terephthalate, ethylene-vinyl acetate copolymer, ethylene-vinyl methylacetate copolymer, ethylene-vinyl ethylacetate copolymer, ethylene-vinyl propylacetate copolymer, polyisoprene, polyacryllonitrile, ethylene-propylene copolymer, and the like.

Contact adhesive layer or lamina 23 directly below rate controlling membrane 16 comprises an adhesive that is essentially free of property of stripping skin cells upon the removal of the medical bandage. Representative adhesives include a mixture of 2-cyanoacrylate and dimethyl methylenemalonate, monomeric ester of alpha-cyanoacrylic acid, cross-linked copolymer of dimethylaminoethylmethacrylate and an alkyl acrylate, adhesive composition comprising a hydrocolloid gum, polyisobutylene and cross-linked dextran, silicone medical adhesive, mineral oil-polyisobutylene adhesive, and the like. The adhesive optionally can contain a rheological agent that imparts thixotropic characteristics to the adhesive, aids in increasing its cohesiveness and bond strength, imparts slump control, maintains the medical bandage on the skin and lets it be easily removed therefrom at the end of the drug delivery period. The rheological agents useful for this purpose, in a presently preferred embodiment, are the silicone compounds, such as fumed silica and the like as presented earlier in the specification. Optionally, the adhesive also can contain a drug, particularly a vasodilator, that is released therefrom as an initial pulse or priming dose, with the system thereafter delivering drug at a substantially constant rate during the duration of the medical treatment. The amount of agent compound homogenously blended into the adhesive is about 0.1% to 20% by weight.

The release liner 24 in contact with adhesive layer 23 and removed just prior to use is exemplified by, in one embodiment the same materials used for the backing member, provided they are removable or made removable by siliconizing the material. Other release liners include siliconized polyester, poly(1,1-dihydroperfluoroctylmethacrylate), fumed silica in silicone rubber, end-capped siliconized polyethylene terephthalate, polytetrafluoroethylene, cellophane, treated paper, siliconized paper, siliconized kraft paper, aluminized paper, paper coated with polyethylene, a film of polyvinyl chloride having titanium dioxide dispersed therein, and the like. The release liner may be formed with dimples for decreasing contacting surface with the adhesive layer, and it may be formed with a pull-tab for making it easier for removing it from the bandage.

The term Freon ® as used herein generically denotes perfluorodimethylcyclobutane; octafluorocyclobutane; perfluorocyclobutane; bromotrifluoromethane; tetrafluoromethane; trifluoromethane; 1,2-dichlorofluoroethane; 1-dichlorofluoro-2-chlorodifluoroethane; 1,2-difluorochloroethane; 1-difluorochloro-2-trifluoroethane; 1,2-trifluoroethane; chlorodifluoromethylmethane; and the like. The term solvent as used herein denotes inert organic solvents such as ethers, lower alkanols, halogenated solvents, petroleum distillate having a boiling range of 60° to 160° C., and the like, such as ethanol, isopropyl alcohol, diethyl ether, chloroform, tetrahydrofuran, and the like.

The following examples are presented for further illustrating the medical bandage of the invention, its manufacture and its rate of release. The examples are not intended to limit the invention in any manner.

EXAMPLE 1

A bandage for the administration of a drug was prepared as follows: first, a drug release rate controlling membrane was prepared by blending 4 kilograms, kg, of ethylene-vinyl acetate copolymer having a vinyl acetate content of 7.5 weight percent, wt %, and 2 kg of ethylene-vinyl acetate copolymer having a vinyl acetate content of 12 wt % in a V-blender to produce a homogenous blend. Next, the blend was fed into an extruder to yield a 0.002 inch 0.05 mm, thick film having a net vinyl acetate content of 9 wt %. A section was cut from the film for use in making the bandage. Then, a silicone medical adhesive solution, in Freon ®-113 solvent, or trichlorotrifluoroethane, containing 18.5% solids, was evaporated until the solid content was 55%, and to this was added 10% isopropyl alcohol. This solution was cast onto one surface of a cut section of ethylene-vinyl acetate copolymer film. The solvent was evaporated in an oven. The film on its removal from the oven had a dry adhesive layer of about 0.0015 to 0.0025 inches, 0.038 to 0.063 mm, thick. After its removal from the oven the silicone adhesive layer was laminated with a protective substrate liner consisting of 0.002 inch, 0.05 mm, thick dimpled polyvinyl chloride film to yield a trilaminate.

Next, a drug reservoir was prepared as follows: first, 55 part of pharmaceutically acceptable 10% nitroglycerin-lactose was dry blended with 1.5 parts of colloidal silicon dioxide and passed through a 40 mesh, 0.42 mm, screen. The blend was transferred to the bowl of a planetary mixer and to this was added 43.5 parts of silicone medical fluid, 100 centistokes. The materials were blended for about one-half hour to yield a homogenous drug reservoir.

Figure 6:
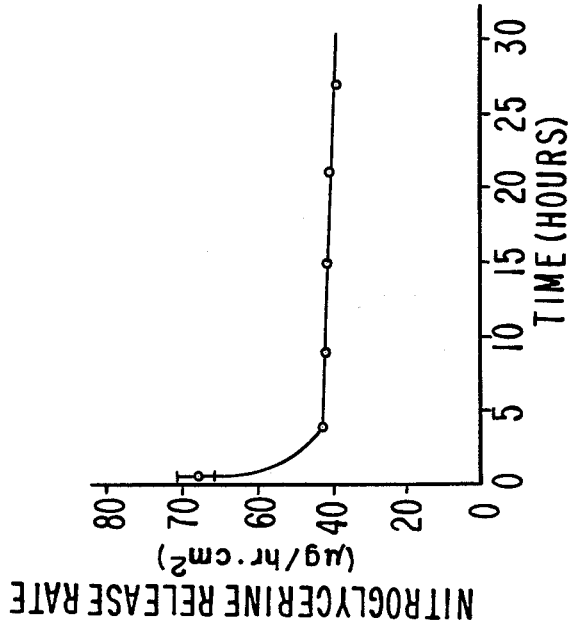
FIG. 6 is a graph depicting the release rate of nitroglycerin from a medical bandage.

Next, a layer of the drug reservoir, about 0.5 mm thick, and containing about 25 mg of nitroglycerin, was deposited onto the other available surface of the ethylene-vinyl acetate copolymer film, while maintaining its outer periphery free of drug reservoir composition. Then a backing member comprising polyethylene terephthalate-aluminum-ionomer-ethylene-vinyl acetate copolymer was laminated to the other surface of the reservoir. The peripheral surface of the backing member extended around the drug reservoir and it was heat sealed to the copolymer of the trilaminate to yield the medical bandage. The medical bandage had an elliptical drug release rate surface that measured 6 cm×2.5 cm nominal, and it was rated to deliver in vitro about 400 μg/hr of nitroglycerin. The nitroglycerin release rate for the medical bandage is depicted in FIG. 6.

EXAMPLE 2

Following the procedure of Example 1, a medical bandage was prepared having an elliptical shape with a drug releasing surface of about 8 cm by 2.7 cm, nominal, a reservoir containing 50 mg of nitroglycerin, and manufactured to deliver in vitro about 800 μg/hr of nitroglycerin.

EXAMPLE 3

Following the procedure of Example 1, a medical bandage was prepared having an elliptical drug releasing surface of about 9 cm by 3.4 cm, nominal, with a drug reservoir containing 75 mg of nitroglycerin, and designed to deliver in vitro about 1200 μg/hr of nitroglycerin.

EXAMPLE 4

Following the procedure of Example 1, a medical bandage was prepared comprising an elliptical drug releasing surface of about 3 cm by 1 cm, nominal, with a drug reservoir containing about 13 mg of nitroglycerin, and rated to deliver about 200 μg/hr of nitroglycerin.

EXAMPLE 5

A drug release rate controlling medical bandage for administering topically a therapeautically effective amount of drug to the skin was prepared as follows: first, three grams, gms, of colloidal silicon dioxide was placed into a blender with 97 gms of medical grade silicone fluid, 100 cs, polydimethylsiloxane, molecular weight about 12,000, and then blended for about 10 minutes to produce a still uniform gel exhibiting Bingham visco properties. Next, the 100 gms of gelled silicone fluid was transformed to a planetary mixer and 100 gms of nitroglycerin adsorbed on lactose comprising 10% active nitroglycerin was added to the mixer. The nitroglycerinlactose was blended into the gelled silicone fluid at a stirring speed of 100 RPM for 10 minutes, to produce a uniform, stable drug reservoir formulation containing 50 mg of nitroglycerin for each gram of reservoir.

Next, a thin layer of silicone medical adhesive solution comprising 18.5% solids in trichlorotrifluoroethane was cast onto cellophane using a casting knife set at 0.012 inches, 0.3 mm, wet gap thickness. The solvent was evaporated in an air current, to yield an adhesive film 0.002 inches, 0.05 mm, thick. Then, an ethylenevinyl acetate copolymer film, having a vinyl acetate content of 9 wt %, and 0.002 inches thick, was laminated to the adhesive film using a two roll laminator. The lamination was done at 50 psig and at a laminating speed of 10 feet per minute.

500 mg of the drug reservoir was placed onto the ethylenevinyl acetate copolymer surface of a backing member. The member comprises ethylene-vinyl acetate copolymer aluminum vapor deposited on polyethylene terephthalate in laminar arrangement with a lamina of high density polyethylene. The periphery of the backing member extended about 3 mm outward from the reservoir. Next, the release liner comprising cellophane adhesive ethylene-vinyl acetate copolymer laminate was positioned over the drug reservoir with its peripheries, about 2 mm, extended outward from the reservoir. The ethylenevinyl acetate copolymer of the liner was placed in contact with the reservoir. The periphery of the backing member was pressed around the reservoir and heat sealed to the copolymer of the liner. The final medical bandage comprises a sealed container containing the reservoir, which reservoir comprises nitroglycerin in gelled silicone fluid. The bandage was designed to release nitroglycerin in vitro at the rate of about 40 μg/hr at 32° C.

EXAMPLE 6

The procedure of Example 1 is followed in this example with all the manufacturing procedures maintained, except that in the medical bandage of this example, the vasodilator is triethanolamine trinitrate.

EXAMPLE 7

A medical bandage is made by following the procedure of Example 5, with the vasodilator in the bandage octyl nitrate.

EXAMPLE 8

A drug reservoir was prepared as follows: first, 727 parts of medically acceptable silicone fluid, 10,000 cs, was blended with 15 parts of fumed silica and 7 parts of amorphous silica in a high shear mixer until a consistent stiff gel was obtained. Then, using low shear, 250 parts of isosorbide dinitrate-lactose was blended into the gel to produce the drug reservoir formulation. The isosorbide dinitrate-lactose comprises 20% of the active drug, isosorbide dinitrate, a vasodilator useful for relaxing smooth muscles in blood vessels, and 80% lactose. The reservoir contained 50 mg of isosorbide dinitrate per gram of gel. The reservoir was used in the procedures of Example 1 and Example 5 for manufacturing medical bandages having round and square shapes respectively. The bandages, in operation, deliver a therapeutically effective amount of the vasodilator for a period greater than 24 hours.

EXAMPLE 9

A medical bandage for administering topically nitroglycerin was made as follows: first, medical grade silicone adhesive in Freon ® solution containing 18.5 wt % solids was cast onto coated, dense Kraft paper, used as a liner substrate, and air dried in an oven. The dry adhesive lamina was about 0.0015 to 0.0025 inches, 0.038 to 0.063 mm, thick. Next, to the adhesive paper laminate, after its removal from the oven, a film of ethylenevinyl acetate copolymer, having a vinyl acetate content of 9% was laminated onto the adhesive laminate.

82 kg of medical silicone fluid, polydimethylsiloxane, 350 cs, was added to a mixer, and the 8 kg of colloidal silicon dioxide was added to the mixer. The fluid and said silicon dioxide were blended at high shear until all the colloidal silicon dioxide was comminuted and well blended to produce a stiff gel. The gel was transferred to a low shear blender, and 110 kg of therapeutically acceptable 10% nitroglycerin on lactose was added to the blender. The blender was turned on, and the ingredients blended to a uniform gel containing 55 mg of nitroglycerin per gram of gel.

Next, a layer of nitroglycerin-silicone gel was deposited onto the other surface of the ethylene vinyl acetate copolymer of the protective liner, while keeping the outer rim of the copolymer free of gel. Then, a backing member comprising pigmented medium density polyethylene-aluminum vapor deposited on polyethylene terephthalate-ethylene vinyl acetate copolymer was laminated to the free surface of the gel. The lamination was carried out under partial vacuum to lessen entrapped air. The peripheral edge of the backing member was pressed around the gel and sealed to the protective liner to yield a self-contained medical bandage. The bandage exhibited a release rate of 400 μg/hr at 32° C.

EXAMPLES 10-12

Following the procedure of example 9, medical bandages were prepared that in vitro exhibited a rate of release of 200 μg/hr of nitroglycerin at 32° C.; 800 μg/hr of nitroglycerin at 32° C.; and 1200 μg/hr of nitroglycerin at 32° C.

EXAMPLE 13

A drug reservoir was prepared as follows: first, 727 parts of medically acceptable silicone fluid, 150 cs, was blended with 15 parts of fumed silica and 10 parts of amorphous silica in a high shear mixer until a stiff gel was produced. Then, using a low shear mixer, 250 parts of isosorbide dinitratelactose comprising 20% of the drug and 80% of lactose was added to the mixer and blended into the gel to produce the drug reservoir.

500 mg of the drug reservoir was placed onto the ethylenevinyl acetate copolymer surface of a backing member. The member comprises ethylene-vinyl acetate copolymer-aluminum coated polyethylene terephthalate-polyethylene laminate. The outer edge of the backing member was pressed downward along the edge of the reservoir, and sealed to a laminate comprising block copolymer of tetramethylene terephthalate-polytetramethylene ether glycol terephthalate-adhesive-cellophane. The copolymer was in contact with the reservoir, and on peeling the cellophane from the bandage, it releases, when in operation a therapeutically effective amount of the vasodilator for treating angina pectoris.

EXAMPLE 14

The procedure of Example 13 was repeated with all conditions as before, except the copolymer in this bandage used for governing the rate of delivery was segmented copolymer of butylene terephthalate 33%, and polytetramethylene ether terephthalate 67%. The medical system, when in operation after the cellophane is stripped therefrom, releases a therapeutically effective amount of the vasodilator for increasing the supply of oxygen to the heart.

EXAMPLE 15

A drug reservoir was prepared as follows: first, 730 parts of medically acceptable silicone fluid, 350 cs, is blended with 15 parts of fumed silica and 15 parts of amorphous silica in a high shear mixer until a still gel was produced. Then, using a low shear mixer, 250 parts of isosorbide dinitratelactose, comprising 20% of the drug and 80% of lactose was added to the mixer and blended into the gel to produce a drug reservoir.

Next, 500 mg of the drug reservoir was placed onto the ethylene-vinyl acetate copolymer surface of a backing member. The member is a laminate comprising ethylene-vinyl acetate copolymer-aluminum coated polyethylene terephthalate-polyethylene. The edges of the backing member were pressed downward along the reservoir and sealed to a drug release rate controlling membrane comprising ethylene ethacrylate having an acrylate content of 18%. The bandage is topically applied to an animal by a strip of tape, an elastomeric arm band, or other mechanical means.

Figure 7:
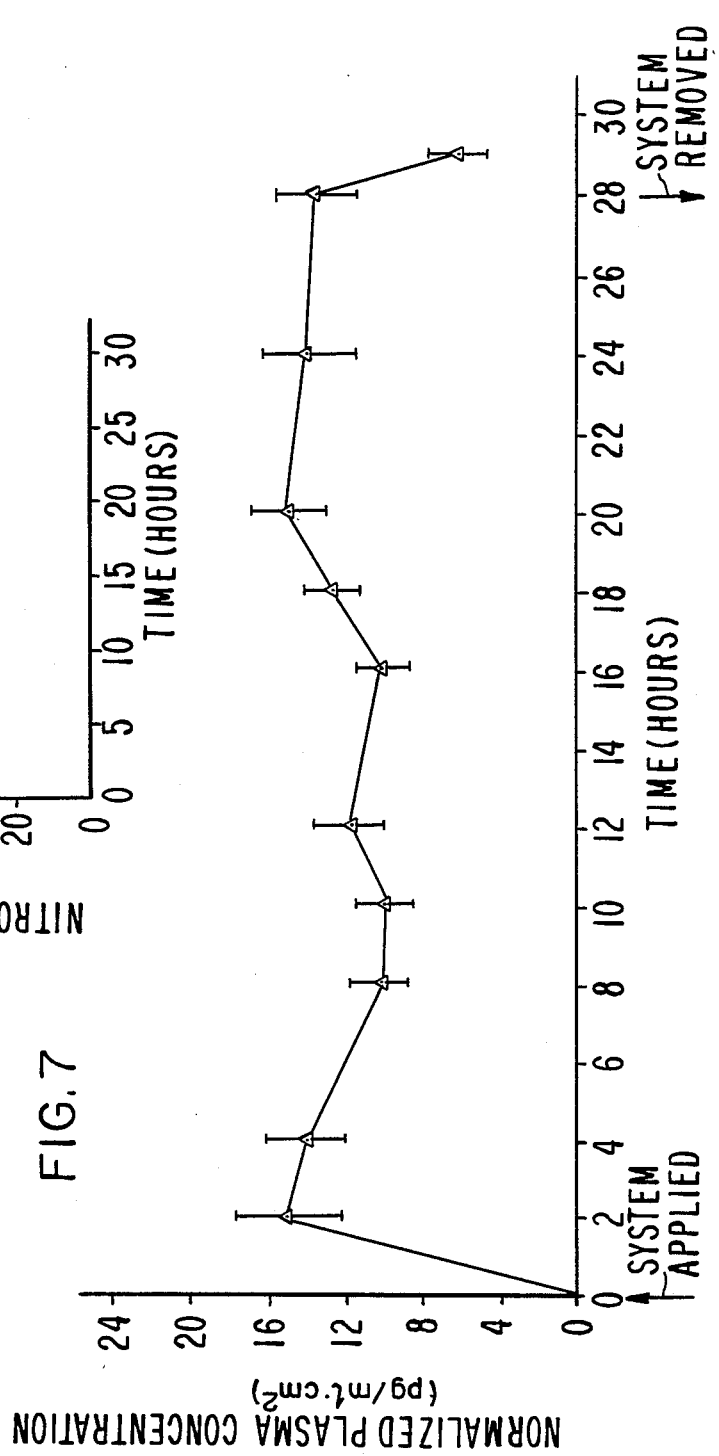
FIG. 7 is a graph depicting the plasma concentration of nitroglycerin afforded by a medical bandage.

The delivery of a vasodilator from a therapeutic delivery system made according to the invention was demonstrated by the following study. A therapeutic delivery system manufactured as a circular shaped medical bandage was used for delivering transdermally the vasodilator. The medical bandage is a laminate comprising from the top on occlusive backing member which member is a laminate comprising high density polyethylene in laminar arrangement with aluminized polyethylene terephthalate and a lamina of ethylene-vinyl acetate copolymer, a reservoir lamina adjacent to the latter copolymer which reservoir comprises medical, gelled silicone fluid, national formulary collodial dioxide and nitroglycerin-lactose, and adjacent to the reservoir a release rate controlling lamina of ethylene-vinyl acetate copolymer, through which nitroglycerin is released from the reservoir after the bandage is affixed to the skin of a human patient. A contact adhesive lamina adjacent to the rate controlling lamina holds the bandage on the skin. A strippable lamina comprising cellophane is adjacent to the contact adhesive, and it is strippped from the bandage before the bandage was placed on the skin. The bandage contained 25 mg of nitroglycerin and it had a steady state in vitro release rate of 400 μg/hr/10 cm$^2$, and it was placed on the arms of twelve volunteer male subjects. FIG. 7 depicts the nitroglycerin plasma concentration, normalized to one cm$^2$ area of application as a function of time for the twelve patients. Other bandages containing from 5 mg to 1000 mg of nitroglycerin produced similar results.

The novel therapeutic transdermal delivery systems of this invention use means for obtaining controlled release rates topically while maintaining the integrity of the system. While there has been described and pointed out features of the invention as applied to presently preferred embodiments, those skilled in the art will appreciate that various modifications, changes, additions and omissions in the systems illustrated and described can be made without departing from the spirit of the invention.

I claim:

1. A medical bandage for administering a drug, said bandage comprising: (1) a backing member defining one face surface of the bandage; (2) a rate controlling membrane formed of a material that meters the flow of a drug from the bandage defining the other face surface of the bandage, and disposed between (1) and (2); (3) a reservoir comprising a gelled fluid, a rheological agent selected from the group consisting of cellulose, polysaccharide, and silicone agents, and a drug.

2. The medical bandage for administering a drug according to claim 1 wherein the backing member contacts the rate controlling membrane to form a fluid-tight bandage.

3. The medical bandage for administering a drug according to claim 1 wherein the backing member is a laminate comprising a lamina of aluminzed polyethylene-terephthalate, a lamina of an ionomer, and a lamina of ethylene-vinyl acetate copolymer.

4. The medical bandage for administering a drug according to claim 1 wherein the backing member is a laminate comprising a lamina of polyethylene, a lamina of aluminized polyethyleneterephthalate and a lamina of ethylene-vinyl acetate copolymer.

5. The medical bandage for administering drug according to claim 1 wherein the rate controlling membrane is ethylenevinyl acetate copolymer.

6. The medical bandage for administering drug according to claim 1 wherein an adhesive is one the rate controlling membrane.

7. The medical bandage for administering drug according to claim 1 wherein the backing member and the rate controlling membrane form a fluid tight bandage, and an adhesive protective liner is in contact through the adhesive with the membrane.

8. The medical bandage for administering drug according to claim 1 wherein the rheological agent is silicon dioxide.

9. The medical bandage for administering drug according to claim 1 wherein the fluid is gelled silicon fluid.

* * * * *